United States Patent [19]
Steber et al.

[11] Patent Number: 5,801,141
[45] Date of Patent: Sep. 1, 1998

[54] IMPLANT COMPOSITIONS CONTAINING A BIOLOGICALLY ACTIVE PROTEIN, PEPTIDE OR POLYPEPTIDE

[75] Inventors: William David Steber, Ewing, N.J.; Susan Mancini Cady; David Farley Johnson, both of Yardley, Pa.; Theresa Rice Haughey, Raleigh, N.C.

[73] Assignee: American Cyanamid Company, Madison, N.J.

[21] Appl. No.: 456,167

[22] Filed: May 31, 1995

Related U.S. Application Data

[63] Continuation-in-part of Ser. No. 97,548, Jul. 26, 1993, abandoned, which is a continuation-in-part of Ser. No. 719,898, Jun. 24, 1991, abandoned.

[51] Int. Cl.$^6$ .......................... A61K 9/24; A61K 38/18; A61K 38/27
[52] U.S. Cl. ...................... 514/2; 424/424; 514/12; 514/21
[58] Field of Search .................... 514/2, 12, 21; 424/422, 424, 426, 463, 471, 472, 473

[56] References Cited

U.S. PATENT DOCUMENTS

| | | | |
|---|---|---|---|
| 3,146,169 | 8/1964 | Stephenson et al. | 424/467 |
| 3,845,770 | 11/1974 | Theeuwes et al. | 424/15 |
| 4,180,560 | 12/1979 | Katz et al. | 424/21 |
| 4,271,113 | 6/1981 | Luschen | 264/112 |
| 4,595,583 | 6/1986 | Eckenhoff et al. | 424/15 |
| 4,612,008 | 9/1986 | Wong et al. | 604/892 |
| 4,624,847 | 11/1986 | Ayer et al. | 424/467 |
| 4,814,181 | 3/1989 | Jordan et al. | 424/473 |
| 4,837,381 | 6/1989 | Steber et al. | 424/502 |
| 4,846,844 | 7/1989 | De Leon et al. | 424/422 |
| 4,855,141 | 8/1989 | Eckenhoff et al. | 424/473 |
| 4,863,736 | 9/1989 | Azain et al. | 424/423 |
| 4,876,094 | 10/1989 | Benton et al. | 424/472 |
| 4,915,953 | 4/1990 | Jordan et al. | 424/473 |
| 4,915,954 | 4/1990 | Ayer et al. | 424/473 |
| 4,917,685 | 4/1990 | Viswanathan et al. | 530/399 |
| 4,959,218 | 9/1990 | Eckenhoff et al. | 424/473 |
| 4,996,060 | 2/1991 | Eckenhoff et al. | 424/473 |
| 5,023,088 | 6/1991 | Wong et al. | 424/473 |
| 5,106,631 | 4/1992 | Turner et al. | 514/21 |
| 5,342,622 | 8/1994 | Williams et al. | 424/425 |

FOREIGN PATENT DOCUMENTS

| | | |
|---|---|---|
| 0246540 | 11/1987 | European Pat. Off. . |
| 0403032 | 12/1990 | European Pat. Off. . |
| 907180 | 9/1990 | South Africa . |
| WO 87/06828 | 11/1987 | WIPO . |
| WO 92/02211 | 2/1992 | WIPO . |

OTHER PUBLICATIONS

Remington's Pharmaceutical Sciences, 17th Edition, pp. 1644–1661 (1985).
Stenesh, Dictionary of Biochemistry and Molecular Biology, 2nd ed., published 1989 by John Wiley & Sons NY), pp. 205, 449.

Primary Examiner—Jeffrey E. Russel
Attorney, Agent, or Firm—Peggy A. Climenson

[57] ABSTRACT

The invention relates to implants for the parenteral administration of an essentially uniform and continuous amount of a biologically active protein, peptide or polypeptide over an extended period of time which comprises a compacted, indented and partially coated composition containing from one to three layers of a homogeneous core mixture comprising about 20% to about 80% of a biologically active protein, a peptide or a polypeptide; about 10% to about 75% of a fat, a wax or a mixture thereof; 0% to about 25% of a buffer, a salt, a sugar or a mixture thereof; 0% to about 15% of a filler, on a weight basis of the total weight of the core mixture. The partial coating of a semipermeable material comprises about 5% to about 50%, on a weight basis of the total weight of the implant. The invention also relates to methods for increasing and maintaining elevated blood levels of biologically active proteins, peptides and polypeptides in animals by the administration of said implants.

40 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GTCATGAAGG AACGCCGCTT C ( 2 ) INFORMATION FOR SEQ ID NO:2:

( i ) SEQUENCE CHARACTERISTICS:
 ( A ) LENGTH: 21 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:2:

GAGAGCAGCG AGGCCTTCTA G    21

IMPLANT COMPOSITIONS CONTAINING A BIOLOGICALLY ACTIVE PROTEIN, PEPTIDE OR POLYPEPTIDE

RELATED U.S. APPLICATION DATA

This application is a continuation-in-part of U.S. application Ser. No. 08/097,548, filed on Jul. 26, 1993, now abandoned, which, in turn, is a continuation-in-part of U.S. application Ser. No. 07/719,898, filed on Jun. 24, 1991, now abandoned.

BACKGROUND OF THE INVENTION

FIELD OF THE INVENTION

The difficulties encountered in the development of methods and compositions which continuously release pharmaceutical preparations in a uniform manner over extended periods of time are well known (see, for example, Remington's Pharmaceutical Sciences, 17th Edition, 1985, pages 1644–1661).

U.S. Pat. No. 4,271,113 discloses a process for forming a passageway in an osmotic device. The oral osmotic devices described therein deliver drug formulations over periods of several hours.

U.S. Pat. No. 4,917,685 discloses a delivery device for the administration of stabilized growth hormones. The devices described therein are shown to deliver growth hormones for only a two week period.

Therefore, there exists a need for the continuous release of biologically active proteins, peptides and polypeptides over extended periods of time.

SUMMARY OF THE INVENTION

The present invention relates to an implant for the parenteral administration of an essentially uniform and continuous amount of a biologically active protein, peptide or polypeptide over an extended period of time which comprises a compacted, indented and partially coated composition containing up to three layers of a homogeneous core mixture comprising about 20% to about 80% of a biologically active protein, a peptide or a polypeptide; about 10% to about 75% of a fat, a wax or a mixture thereof; 0% to about 25% of a buffer, a salt, a sugar or a mixture thereof; and 0% to about 15% of a filler, on a weight basis of the total weight of the core mixture. The partial coating of a semipermeable material comprises about 5% to about 50%, on a weight basis of the total weight of the implant.

Surprisingly, it has been found that increased blood levels of biologically active proteins, peptides and polypeptides may be obtained and maintained for extended periods of time by implanting animals with the compacted, indented and partially coated compositions of the present invention.

BRIEF DESCRIPTION OF THE DRAWINGS

The background of the invention and its departure from the art will be further described hereinbelow with reference to the accompanying drawings, wherein.

DETAILED DESCRIPTION OF THE INVENTION

Figure 1:
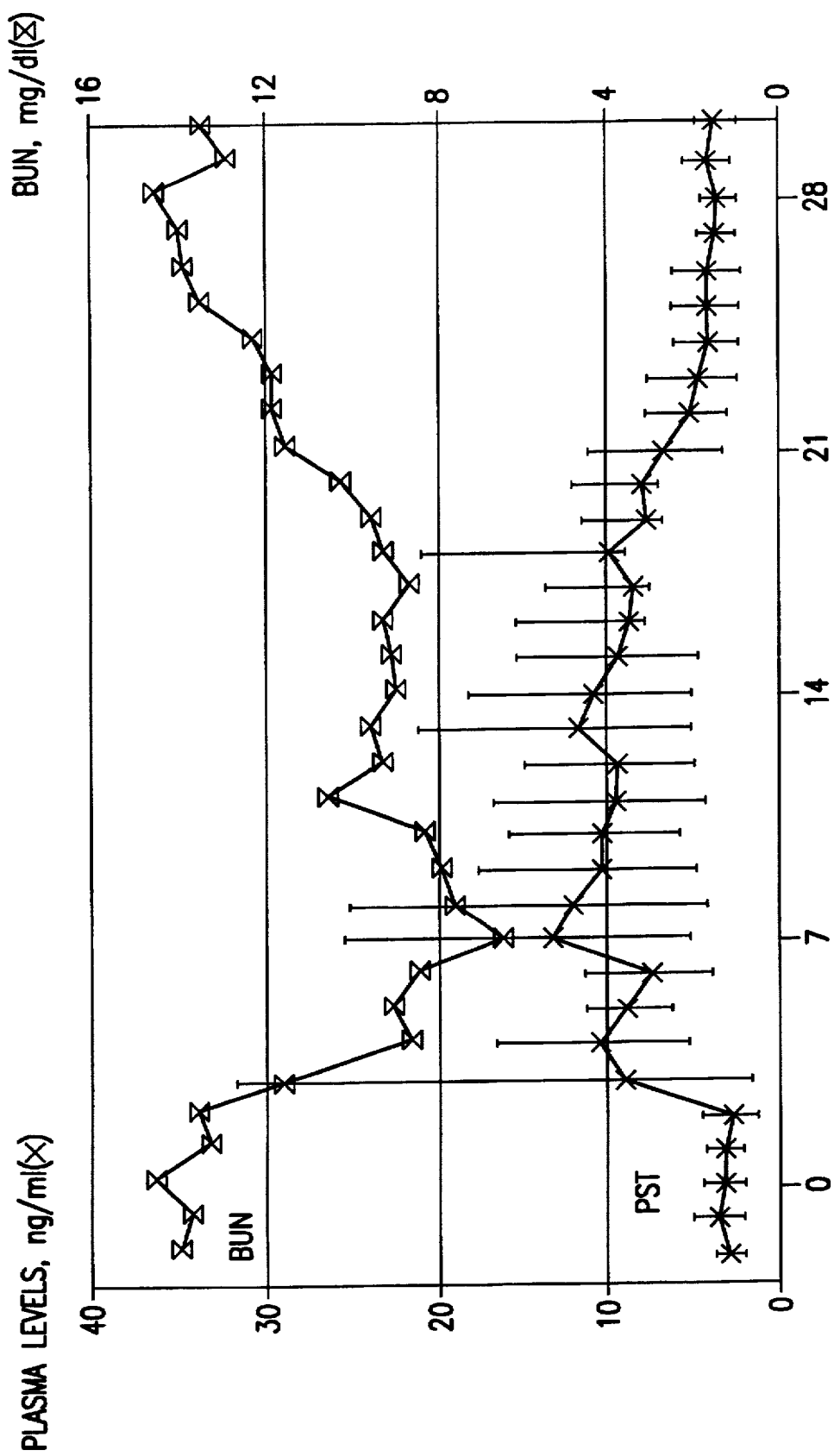
FIG. 1 shows the measurement of the plasma levels of recombinant porcine somatotropin (A6TS11R+E34 rpST) and blood urea nitrogen (BUN) in a group of seven pigs. Pigs are implanted on Day 0 with three implants having core weights of 60 mg, 90 mg and 90 mg, and a coating thickness of 4 mil, 9.2 mil and 9.2 mil, respectively. The data represent the geometric mean plasma levels of the rpST along with the variability in the pigs expressed as mean plus or minus the standard deviation. Also shown are mean BUN levels taken from the blood samples of each of the animals.

The implant of the present invention comprises a compacted, indented and partially coated composition containing from one to three layers of a homogeneous core mixture, each layer of which has about 20% to about 80% of a biologically active protein, a peptide or a polypeptide; about 10% to about 75% of a fat, a wax or a mixture thereof; 0% to about 25% of a buffer, a salt, a sugar or a mixture thereof; and 0% to about 15% of a filler, on a weight basis of the total weight of the core mixture.

A more preferred implant of this invention is a compacted, indented and partially coated composition containing a homogeneous mixture of about 45% to about 65% of the biologically active protein, the peptide or the polypeptide; about 15% to about 50% of the fat, the wax or the mixture thereof; about 2% to about 20% of the buffer, the salt or the mixture thereof; and about 1% to about 15% of the filler, on a weight basis of the total weight of the core mixture.

Biologically active proteins, peptides and polypeptides suitable for administration in the compositions of the present invention include growth factors, the biologically active fragments and derivatives thereof, and somatomedins. Preferred proteins include the somatotropins such as porcine, ovine, equine, bovine, avian and human somatotropins; and is meant to encompass those which are of natural, synthetic, recombinant or biosynthetic origin. It is further contemplated that use of the term "somatotropin" embraces all synonymous proteins such as phyone, somatotropic hormone, growth hormone (such as, for example, adenohypophyseal growth hormone, hypophyseal growth hormone, anterior pituitary growth hormone, etc.) and the like. More preferred proteins are somatotropins with alterations in the α-helix 1 region, the α-helix 2 region, the α-helix 3 region or combinations thereof, and other mutations, such as E34 rpST, I122L+E34 rpST and A6TS11R+E34 rpST which are mutants of the natural form of pituitary porcine somatotropin. Pituitary pST is a single-chain polypeptide with two intrachain disulfide bridges at cystine 52–163 and cystine 180–188. The primary structure of pituitary pST isolated from porcine pituitaries contains 190 amino acids having phenylalanine at the amino terminus. In the E34 rpST mutant, both cysteine 183 and cysteine 191 are converted to glutamic acid. For combination mutant I122L+E34, the isoleucine at position 122 is replaced with leucine and is combined with the E34 mutations. Additionally, the cysteines in the small loop of the recombinant somatotropins can be chemically derivatized with various substituents to form modified mutants such as carbimidomethyl rpST.

Most preferred, the combination mutant A6TS11R+E34 rpST combines the double mutation A6TS11R, in which the alanine at position 6 is replaced with threonine and the serine at position 11 is changed to arginine, is combined with the E34 mutations. Also, the first three amino acids (Met, Asp and Gln) are attached to phenylalanine which is the amino terminus of pituitary pST. The recombinant porcine somatotropin, A6TS11R E34 rpST, has a molecular formula of $C_{996}H_{1556}N_{271}O_{298}S_6$ and a molecular weight of 22,254. The cysteine substitution is made to eliminate the intrachain disulfide bridge (cystine) which has been found to be susceptible to cleavage and reformation as an interchain disulfide bridge with another pST molecule under the conditions found in a sustained release system. The resulting dimer is not biologically active and has been found to block the release of material from sustained release systems. The alanine to threonine and serine to arginine substitutions are made to reduce the tendency of the molecule to form insoluble, biologically inactive aggregates in a sustained release system.

The E. coli bacterial strains carrying the plasmids E34 rpST, I122L+E34 rpST and A6TS11R+E34 rpST are deposited in American Cyanamid Company's culture collection maintained in Princeton, N.J. and are also deposited pursuant to the Budapest Treaty with the American Type Culture Collection (ATCC), 12301 Parklawn Drive, Rockville, Md. 20852, U.S.A., under deposit accession numbers ATCC 67764, ATCC 67768 and ATCC 67772 for three different E. coli strains carrying the same E34 rpST plasmid, ATCC 68417 for the E. coli strain carrying the I122L+E34 rpST plasmid and ATCC 68412 for the E. coli strain carrying the A6TS11R+E34 rpST plasmid.

The above-described recombinant somatotropins are prepared by site directed mutagenesis, but other conventional means such as chemically synthesizing the peptides or proteins may be employed in producing said somatotropins. Modifications may involve replacing one to four of the cysteine amino acid residues of the animal somatotropins by one to four amino acid residues, for example, arginine, lysine, aspartic acid, glutamic acid, asparagine, glutamine, histidine, alanine, glycine, isoleucine, leucine, valine, phenylalanine, tryptophan, tyrosine, methionine, serine, threonine or proline. Modifications may also involve converting all four cysteines to cysteic acid.

Currently utilized techniques for the alteration of the DNA sequence of a cloned segment of DNA at a specific defined site require the production of a single stranded form of that DNA. The single stranded DNA is annealed to a synthetic oligonucleotide which is complementary to a portion of that DNA except that the oligonucleotide contains within it a region of mismatch. The region of mismatch is usually located in the central portion of the oligonucleotide. In some instances, the oligonucleotide also contains a restriction endonuclease recognition site at or near the site of mutation. The annealed mixture is then made double stranded and covalently closed by the addition of E. coli DNA polymerase I, large fragment and deoxynucleotide triphosphates in the presence of T4 DNA ligase and adenosine 5' triphosphate. The double stranded DNA is then transformed into an appropriate E. coli strain where the mismatched region of the DNA is repaired and replicated.

Two populations of clones are obtained. Depending on which strand is chosen as the template for repair synthesis, a clone either contains the wild type or the altered (mutated) sequence. The clones which contain the mutated sequence, that which corresponds to the sequence of the oligonucleotide, are selected by hybridization to the radioactively-labeled oligonucleotide. Due to mismatch between the oligonucleotide and the wild type sequence, the radioactively-labeled oligonucleotide is more stably bound to the clones which contain the mutated sequence. Incubation at an appropriate temperature discriminates between wild type and mutated clones. When the oligonucleotide also contains a restriction endonuclease cleavage site, digestion of candidate clones with the cognate restriction endonuclease reveals clones which contain the mutated sequence and provides another means of discriminating between wild type and mutated clones. The alterations in the identified clones then are confirmed by DNA sequencing of the relevant regions.

Restriction fragments of plasmid clones containing the desired mutation are reconstructed into expression plasmids suitable for expressing the mutant gene product in either bacteria or yeast, but not both. This reconstruction is achieved by standard subcloning procedures.

To prepare E34 rpST, substitution of the cysteines in the small loop disulfide bond is accomplished using long synthetic oligonucleotides designated GLU3 and GLU4 which have the following sequences (corresponding to Sequence I.D. Nos. 1 and 2):

```
5' GTC ATG AAG GAA CGC CGC TTC 3' GLU3
                GLU
5' GAG AGC AGC GAG GCC TTC TAG 3' GLU4
                GLU
```

This alters the sequence of the rpST gene such that the codon for cysteine at position 183 is converted from TGT to GAA which codes for glutamate and the cysteine at position 191 is converted from TGT to GAG which also codes for glutamate. Thus, the cysteines in the small loop are both converted to glutamate. Single stranded M13mp11pST DNA is prepared from purified phage by standard protocols. 1000 ng of single stranded M13mp11pST DNA is mixed with 50 ng each of GLU3 and GLU4 oligonucleotides, which have previously been 5' phosphorylated with adenosine 5' triphosphate and polynucleotide kinase in a final volume of 10 μL containing 1× annealing buffer (1× annealing buffer is 75 mM KCl, 5 mM trs, pH 8.0). The mixture is heated at 65° C. for 7 minutes and then kept at room temperature for 10 minutes. This protocol anneals the oligonucleotide to the single stranded DNA. The annealed DNA is then converted to a double stranded covalently closed form by the addition of 20 μL H$_2$O, 4 μL 10× fillin buffer (1× fillin buffer is 275 mM MgCl$_2$, pH 7.5, 2 mM DTT), 1 μL 20 mM ATP, 2 μL dNTP's (a mixture of the four deoxyribonucleotide 5' triphosphates each at a concentration of 2 mM), 2 U T4 DNA ligase and 2 U DNA polymerase I large fragment (for unit definition, see New England Biolabs catalogue, 1986). The mixture is incubated for 1 hour at room temperature. The mixture is then transformed into E. coli JM101 by a standard calcium chloride procedure. After overnight incubation at 37° C. plaques can be seen on a lawn of JM101. The plaques are lifted in duplicate onto nitrocellulose filters and processed for hybridization by standard protocols. Each lift is hybridized separately to either $^{32}$P labeled GLU3 or GLU4. They are radioactively labeled at the 5' end with d-$^{32}$P-ATP and polynucleotide kinase. Hybridization is overnight at 37° C. in 5×SSC, 1× Denhardt's, 150 μg/mL tRNA. The filters are washed sequentially in 5×SSC at 4° C., TAC at 37° C. and finally in TAC at the desired temperature. This last wash determines the specificity. For GLU3 and GLU4, the temperature is 56.0° C. After exposure to x-ray film only those plaques which are positive for both oligonucleotides are picked. DNA sequencing reveals that both Cys 183 and Cys 191 are converted to glutamic acid. The clone is designated M13mp11pSTE34 (ATCC accession number 40482).

The altered (mutant) clone is reconstructed into the bacterial expression plasmid pRO211 (ATCC accession number 40483). The M13 clone is cut with EcoRI and HindIII and the pST gene fragment is isolated. pRO211 is digested with the same enzymes treated with calf intestinal alkaline phosphatase and the large fragment is isolated. The two pieces are ligated together with T4 DNA ligase and transformed into an appropriate bacterial strain, for example, E. coli N99cI$^+$. In this strain, a wild type k repressor is present. This prevents expression from the $P_2$ promoter in pRO211. Once the appropriate construction has been isolated, it is then transferred into bacterial strains which contain a temperature sensitive k repressor, e.g. E. coli 4200 (ATCC accession number 67766). In these strains, the expression of rpST is dependent on temperature. At 42° C., the repressor is inactive and expression occurs. At this stage, rpST can be prepared by conventional procedures. Any appropriate E. coli strain, besides the 4200, can be utilized for expression of the pST gene product.

In the construction of the α-helix 3 region combination mutant I122L+E34 rpST, the mutation I122L, in which the isoleucine at position 122 is replaced with leucine, is combined with the E34 mutations in which the DNA encoding cysteine at positions 183 and 191 are replaced with glutamic acid. The I122L mutation can be introduced into the rpST gene by conventional site-directed mutagenesis utilizing an application of polymerase chain reaction technology. The resultant rpST gene contains a mutation in both the α-helix 3 for the mutation I122L and the COOH-encoding regions for the mutation E34. The altered, small rpST-containing EcoRI/SmaI fragment from pROpST-SXA-I122L (ATCC accession number 68418), which contains the I122L mutation, is joined to the large EcoRI/SmaI fragment from plasmid pROpSTE-$T_1T_2$. The resulting plasmid is designated pROpST-SXE-I122L (ATCC accession number 68417).

Similarly, α-helix 1 combination mutant A6TS11+E34 can be constructed. Double mutation A6TS11R, in which the alanine at position 6 is replaced with threonine and the serine at position 11 is replaced with arginine, is combined with the E34 mutations, in which the DNA encoding cysteine at positions 183 and 191 are replaced with glutamic acid. The resultant rpST gene contains mutations in both the $NH_2$-(A6TS11R) and COOH-encoding regions (E34) of the rpST DNA. The altered, small, rpST-containing EcoRI/SmaI fragment from pML/pGH14, which contains the A6TS11R mutations, is joined to the large EcoRI/SmaI fragment from plasmid pROpSTE-$T_1T_2$. This latter plasmid is the pST expression plasmid, which also contains the strong transcription terminator from the *E. coli* rrnB operon ($T_1T_2$) at the 3' end of the rpST-encoding DNA. The resulting plasmid is designated pROpSTE-A6TS11R (ATCC accession number 68412).

Derivatized recombinant somatotropins are prepared by dissolution or dispersion of the somatotropin in water or an aqueous solution of guanidine hydrochloride, sodium bicarbonate or the like, which is adjusted to pH 8.4 with aqueous base such as sodium or ammonium hydroxide. To this solution is then slowly added dithiothreitol, i.e., DL-threo-1,4-dimercapto-2,3-butanediol. The addition is generally conducted under an atmosphere of nitrogen at room temperature. To the resulting solution is then added iodoacetamide, iodoacetic acid, sodium tetrathionate, methyl methanethiosulfonate, 1,3-propane sulfone or other derivatizing agent. The mixture is stirred for about one to four hours, then desalted by ultrafiltration. The solution is concentrated and then subjected to several cycles of redilution with water, aqueous guanidine hydrochloride or the like, followed by ultrafiltration. The residue from the final filtration is then lyophilized to yield the derivatized rpST.

Waxes and fats which are suitable for use in the composition of the present invention in general have melting points higher than 40° C. The wax of the invention may be defined as set forth in Hawley's *The Condensed Chemical Dictionary*, Eleventh Edition, as a low-melting organic mixture or compound of high molecular weight, solid at room temperature and generally similar in composition to fats and oils except that it contains no glycerides. Some are hydrocarbons; others are esters of fatty acids and alcohols. These compounds, classified among the lipids, include saturated or unsaturated long chain $C_{10}$–$C_{24}$ fatty acids, alcohols, esters, salts, ethers or mixtures thereof. The waxes are thermoplastic, but since they are not high polymers, they are not considered in the family of plastics. Common properties are water repellency, smooth texture, nontoxicity, freedom from objectionable odor and color. They are combustible, have good dielectric properties, are soluble in most organic solvents and are insoluble in water.

The major types are as follows:

I. Natural
1. Animal (beeswax, lanolin, shellac wax, Chinese insect wax)
2. Vegetable (carnauba, candelilla, bayberry, sugarcane)
3. Mineral
   (a) Fossil or earth waxes (ozocerite, ceresin, montan)
   (b) Petroleum waxes (paraffin, microcrystalline slack or scale wax)

II. Synthetic
1. Ethylenic polymers and polyol ether-esters (CARBOWAX®, a polyethylene glycol available under the registered trademark of Union Carbide Company)
2. Chlorinated naphthalenes (HALOWAX®, chlorinated naphthalenes of varying chlorine content available under the registered trademark of Koppers Industries, Inc.)
3. Hydrocarbon type via Fischer-Tropsch synthesis The fat of the present invention may be defined as set forth in Hawley's *The Condensed Chemical Dictionary*, Eleventh Edition, as a glyceryl ester of higher fatty acids such as myristic, stearic, palmitic and the like (i.e., glyceryl trimyristate, glyceryl tristearate, glyceryl tripalmitate, etc.). Such esters and their mixtures are solids at room temperatures and exhibit crystalline structure. Lard and tallow are examples. There is no chemical difference between a fat and an oil, the only distinction being that fats are solid at room temperature and oils are liquid. The term "fat" usually refers to triglycerides specifically, while "lipid" is all-inclusive.

The fat is preferably composed of mono-, di- or triglyceryl esters of long chain $C_{10}$–$C_{24}$ fatty acids. The mono-, di-, or triglycerides are composed predominantly of myristates, stearates, palmitates, laurates, linoleates, linolenates, oleates, and residues or mixtures thereof, having melting points greater than 50° C., being most preferred. Glyceryl trimyristate is a most preferred fat.

Certain compositions of unstable, water-insoluble proteins or polypeptides such as somatotropin require the addition of buffers, salts, sugars and comparable adjuvants to provide stability and sustained release activity, with the buffers and salts preferred. Buffers are added to the implant compositions of the present invention to adjust the pH of the composition to a value of from about 6.0 to about 8.5 to effect the solubility of the somatotropin and consequently the release of the somatotropin from the implant composition. Buffers suitable for use in the compositions of the invention include sodium and potassium phosphates, borates, citrates, tartrates, carbonates, glycinates and the like or mixtures thereof, with a mixture of sodium borate, monobasic sodium phosphate and dibasic sodium phosphate being preferred to adjust the pH of the compositions to a preferred value of from about 6.5 to about 8.0.

Salts suitable for use in the composition of this invention include salts such as sodium chloride, calcium chloride, potassium chloride and the like.

Sugars suitable for use in the composition of the present invention include mono-, di- or trisaccharides such as glucose, mannose, sorbitol, mannitol, lactose, sucrose, maltose, cellobiose and raffinose. Preferred sugars are non-reducing mono-, di- or trisaccharides with sucrose, raffinose, sorbitol and mannitol being most preferred.

Excipients which are useful for compacting the core mixture of the present invention in the tableting process include talc such as microcrystalline talc, fumed silica and comparable fillers. Typically, the tableting aid may be added in amounts, on a weight basis, ranging from about 1% to about 15%.

Additives such as antioxidants, preservatives, binders, surf actants or mixtures thereof may be included in the compositions of the invention. Preferred additives include butylated hydroxytoluene (BHT), butylated hydroxyanisole (BHA), sodium nitrite, sodium nitrate, salicylanilide, dehydroacetic acid, sorbic acid, boric acid, benzoic acid and salts thereof, hydroxypropyl cellulose, hydroxypropylmethylcellulose, polyoxypropylene-polyoxyethylene block copolymers (e.g., PLURONIC® ACID F127, commercially available from BASF Corporation, Parsippany, N.J.), etc. The amounts of said additives suitable for use in the invention range from about 0.1% to about 20% on a weight basis.

The compacted and indented compositions are partially coated with one or two layers of a semipermeable material to form the implant of the invention. On the basis of the total weight of the implant, the coating is present in the implant in the amount of about 5% to about 50% while the core ingredients are present in the implant in the amount of about 50% to about 95%. Preferably, the coating is present in the implant in the amount of about 10% to about 39% and the core is present in the amount of about 61% to about 90%.

Semipermeable materials suitable for coating the compressed and indented compositions of the present invention include semipermeable polymers such as methacrylate ester or methacrylic acid copolymers, ethyl or methyl cellulose polymers and the like. Usually, the amount of the polymer ranges, on a weight basis of the dry weight of the coating, from about 65% to about 85% and preferably from about 70% to about 80%. Additives such as plasticizers and fillers may optionally be added to the semipermeable polymers in amounts of about 1% to about 20%, on a weight basis, with triethyl citrate and talc being a preferred plasticizer and filler, respectively. If the final product is sticky to the touch, a tackiness control agent such as talc, and preferably, microcrystalline talc, and the like may be added to the coating in varying amounts, but typically in the amount of about 15% to about 35% and preferably from about 20% to about 30%, on a weight basis of the dry weight of the coating. Additives such as talc may be used as both the filler and the tackiness control agent in an amount up to about 55% or even higher, if desired. To alter the permeability of the coating, methyl cellulose, ethyl cellulose and the like may optionally be added to the polymeric coating for permeation control in the amount, on a weight basis, of about 0.5% to about 3%. A colorant such as the FD&C lakes may also be added, if desired, in the amount of 0% to about 5%, on a weight basis. The thickness of each coating surrounding the compacted and indented compositions is typically from about 0.5 mil to about 25 mil and more typically, from about 2 mil to about 20 mil. Optionally, an antibiotic, such as tetracycline, chlortetracycline and the like, may be applied by dusting, for example, to the coating to reduce the incidence of infection at the site of insertion into the animals.

The term "partial coating" refers to the fact that a substantial portion of the core mixture is covered by the coating with the exception of the indentation in order to provide for the sustained release of the active ingredient through the opening. Using the conventional coating machines, the end of the implant having the indentation will get coated but the coating on the indented side gradually tapers off into the indentation to provide a portion of the indentation with essentially no coating. For adequate control of the release of the active ingredient, the opening to the indentation must not get blocked with the coating.

Surprisingly, it has been found that increased blood levels of the active ingredient, such as the somatotropins, may be obtained and maintained for extended periods of time by using the implant of the present invention. Elevated blood levels of the biologically active proteins, peptides and polypeptides are generally observed for at least about three weeks or longer. The elevated blood levels are associated with beneficial, therapeutic effects which include weight gain, increased growth rate, improved feed efficiency, decreased body fat, improved lean meat to fat ratio, improved muscle size and increased milk production in lactating animals. Maintaining the elevated blood levels is an indication of the slow release of the active ingredient. Properties such as increased growth rate, improved feed efficiency, increased lean meat and increased milk production are generally observed when elevated blood levels of the active ingredient is maintained. The invention includes the use of the compositions herein to increase growth rate, improve feed efficiency, increase lean meat in animals, improve milk production and increase and maintain levels of somatotropins in the blood stream of animals.

The implants of the present invention may be prepared or employed in a variety of ways to achieve the desired sustained release effects. In one method, a single implant may contain two or three layers of the homogeneous core mixture where the amount of the active ingredient may be greater in the middle layer than the layer near to the indentation and even greater in the layer farthest away from the end having the indentation. With three layers, for example, the composition of this invention may provide a first layer of the homogeneous mixture which is placed into a suitable mold first, a middle layer and then a third layer which is put into the mold last, in which the third layer surrounds and is contiguous with the indentation; the middle layer is contiguous with the first and third layers; and the first layer is contiguous with the middle layer and may contain a greater amount of the active ingredient than the third layer.

Alternatively and more preferably, the application of the implants of the invention involves the concomitant use of two or three implants each of which contain the single homogeneous mixture as the core composition. In the case of porcine somatotropin, as an example, one pig dose may comprise two implants having core weights of 60 mg and 90 mg, respectively. Or, one pig dose may consist of three implants having core weights of 60 mg, 90 mg and 120 mg or 60 mg, 90 mg and 90 mg. Additionally, the implant system may employ the same administration of three implants which provide different release profiles for a continuous release of active ingredient from early to late phase of release. By varying the degree of thickness of the coating, the amount of the core ingredients and the indent geometry (i.e., width, depth, shape, extent of taper, etc.), the release profile of the active ingredient may be altered and therefore controlled to obtain the desired daily release rate. For instance, a fast implant in the dimensions of about 4.2 mm×4.8 mm which has 30 mg of somatotropin and 4 mil coating may be used in combination with two slow implants in the dimensions of about 4.5 mm×6.8 mm which each have 45 mg of somatotropin and 9 mil coating to achieve an essentially uniform and continuous release of about 3 mg to about 6 mg of somatotropin on a daily basis.

The implant of the present invention useful for the administration of a biologically active protein, peptide or polypeptide may be prepared by incorporating the active ingredient; buffer, salt or mixture thereof; talc and optionally sugar, with a molten fat, wax or mixture thereof to obtain a coarse powder. Compacted and indented compositions are then prepared with a tablet press set up with conventional implant sizes such as 5/32, 1/8 inches and the like using a special top punch. The top punch has a tapered projection on the center line of the punch which will form a conical indentation in the composition when compressed. Since altering the dimensions of the opening will influence the rate of release, the size of the top punch may be varied to a great extent, dependent upon the desired results. It should be appreciated that any conventional means for providing the hole and/or indentation in the implant, such as punching, drilling, laser treatment and the like, is contemplated as being included in this invention.

One to three layers of the coarse or granulated powder is then placed into the die and compressed with the special top punch to form compacted and indented compositions. In one embodiment of the invention, the amount of biologically active protein, peptide or polypeptide present in each layer increases away from the end having the indentation. The compacted and indented compositions are then partially coated with one or two layers of a semipermeable material to form the implant of the invention. The indentation remains essentially uncoated and becomes a passageway for the active ingredient to exit the composition of the invention over an extended period of time.

In order to facilitate a further understanding of the invention, the following examples are presented to illustrate more specific details thereof. The invention is not to be limited thereby except as defined in the claims.

EXAMPLE 1

Preparation of the Implants of the Present Invention for the Parenteral Administration of Somatotropins The implants of the present invention may be prepared as follows:

1. Preparation of somatotropin, sugar, buffer and additives in a size range suitable for incorporation in the fat, wax or mixture thereof by spray drying may be accomplished by dissolving the somatotropin and sugar in water and then adding the desired buffer solution such as a 1:2 mixture of monobasic and dibasic sodium phosphate. Additives such as hydroxypropyl cellulose may be added and allowed to dissolve. The solution is then spray-dried in a Buchi mini spray drier, model #190.
2. Preparation of granular powder. A homogeneous mixture of the spray dried powder in the molten fat, wax or mixture thereof is prepared and the resulting mixture is cooled to give a powder. The powder is tableted using a Stokes model #512 tablet press set up with 5/8 inch punches and dies. These tablets are milled using a bench-top Glen Mills Microhammer Mill to form a coarse granular powder.
3. Preparation of compacted and indented compositions. Layered, compacted and indented compositions are made with a Stokes model #521 single tablet press set up with a 5/32 inch die and special top punch. The top punch has a 3 mm tapered projection on the center line of the punch. The base of the projection is about 1 mm. To make layered, compacted and indented compositions, the inner end granular powder is placed into the die first and lightly tapped to compress the powder, then the indent end granular powder is placed into the die. The press is operated by hand, so that each implant is made one at a time. To make uniform implants, a 1/8 inch die and special top punch is used. The top punch has a 3 mm tapered projection on the center line of the punch and the base of the projection is about 1 mm. The desired amount of granular powder is placed into the die and the uniform, compacted and indented compositions are prepared by operating the press by hand.
4. Preparation of partially coated implant compositions. The compacted and indented compositions are coated with one or two layers of a semipermeable polymeric material using a MINI HI-COATER® (trademark of Vector Laboratories). The surface within the indentation remains essentially uncoated and becomes a passageway for the active ingredient to exit the composition of the invention over an extended period of time.

Utilizing the above procedure with the materials listed in Table I below yields the implant compositions listed in Table II below.

TABLE I

Somatotropin a. I122L + E34 rpST
b. E34 rpST
c. A6TS11R + E34 rpST
d. carbimidomethyl rpST (CAM − rpST)
e. bovine somatotropin Fat or Wax f. glyceryl trimyristate
g. glyceryl tristearate Sugar h. sucrose
i. lactose Buffer j. 1:2 mixture of monobasic and dibasic sodium phosphate
k. monobasic sodium phosphate
l. sodium borate Additive m. hydroxypropyl cellulose Coating n. poly(ethylacrylate, methylmethacrylate) (EUDRAGIT ® NE30D) containing 8% by weight talc
o. poly(ethylacrylate, methylmethacrylate) (EUDRAGIT ® NE30D) containing 15% by weight talc
p. poly(ethylacrylate, methylmethacrylate) trimethylammonioethylmethacrylate chloride (EUDRAGIT ® RL30D) containing 15% by weight triethyl citrate
q. poly(ethylacrylate, methylmethacrylate) trimethylammonioethylmethacrylate chloride (EUDRAGIT ® RS30D) containing 15% by weight triethyl citrate EUDRAGIT ® is a trademark of Rohm Pharma GmbH.

TABLE II

Implant Compositions

| Composition | | Somatotropin % w/w | Fat or Wax/ % w/w | Sugar/ % w/w | Buffer/ % w/w | Additive/ % w/w | Layer weight (mg) | First Coating/ mil | Second Coating/ mil |
|---|---|---|---|---|---|---|---|---|---|
| 1 | RE[1] | a/35.0 | f/50.0 | h/12.5 | j/2.5 | — | 30 | p/2 | n/5 |
|   | IE[2] | a/70.0 | f/17.6 | h/8.2 | j/4.1 | — | 90 | | |
| 2 | RE | a/35.0 | f/50.0 | h/12.5 | j/2.5 | — | 50 | p/2 | n/5 |
|   | IE | a/70.0 | f/17.6 | h/8.2 | j/4.1 | — | 80 | | |
| 3 | RE | a/35.0 | f/50.0 | h/12.5 | j/2.5 | — | 30 | p/2 | n/5 |
|   | IE | a/65.0 | f/23.5 | h/7.6 | j/3.8 | — | 90 | | |
| 4 | RE | a/35.0 | f/50.0 | h/12.5 | j/2.5 | — | 20 | p/2 | n/5 |
|   | IE | a/65.0 | f/23.5 | h/7.6 | j/3.8 | — | 90 | | |
| 5 | RE | a/40.0 | f/50.0 | h/7.5 | j/2.5 | — | 50 | p/2 | n/5 |
|   | IE | a/70.0 | f/17.6 | h/8.2 | j/4.1 | — | 80 | | |
| 6 | RE | a/40.0 | f/50.0 | h/7.5 | j/2.5 | — | 50 | p/2 | n/5 |
|   | IE | a/65.0 | f/23.5 | h/7.6 | j/3.8 | — | 80 | | |
| 7 | RE | a/40.0 | f/20.0 | h/20.0 | j/4.0 | m/16.0 | 10 | p/2 | n/5 |
|   | IE | a/55.0 | f/31.0 | h/10.3 | j/3.4 | — | 110 | | |
| 8 | RE | a/40.0 | f/20.0 | h/20.0 | j/4.0 | m/16.0 | 20 | p/2 | n/5 |
|   | IE | a/55.0 | f/31.3 | h/10.3 | j/3.4 | — | 100 | | |
| 9 | RE | a/35.0 | f/30.0 | h/17.5 | j/3.5 | m/14.0 | 20 | p/2 | n/5 |
|   | IE | a/55.0 | f/31.3 | h/10.3 | j/3.4 | — | 100 | | |
| 10 | RE | b/40.0 | f/50.0 | h/7.5 | j/2.5 | — | 50 | n/5 | — |
|    | IE | b/65.0 | f/18.7 | h/12.2 | j/4.1 | — | 70 | | |
| 11 | RE | b/50.0 | f/37.5 | h/9.4 | j/3.1 | — | 40 | q/2.5 | o/6 |
|    | IE | b/60.0 | f/25.0 | h/11.3 | j/3.8 | — | 80 | | |
| 12 | RE | c/45.0 | f/43.8 | h/8.4 | j/2.8 | — | 40 | p/1 | n/7 |
|    | IE | c/60.0 | f/25.0 | h/11.3 | j/3.8 | — | 80 | | |
| 13 | RE | c/50.0 | f/37.5 | h/9.4 | j/3.1 | — | 40 | q/2 | o/6 |
|    | IE | c/60.0 | f/25.0 | h/11.3 | j/3.8 | — | 80 | | |
| 14 | Uniform | a/53.8 | g/31.2 | i/13.5 | k/1.5 | — | 80 | n/5 | |
| 15 | Uniform | d/55.0 | f/31.3 | h/10.3 | j/3.4 | — | 120 | q/1 | o/6.5 |
| 16 | RE | c/50.0 | f/44.4 | — | j/4.4 l/1.1 | — | 40 | q/1 | o/6.5 |
|    | IE | c/60.0 | f/33.3 | — | j/5.3 l/1.3 | — | 90 | | |
| 17 | RE | e/50.0 | f/37.5 | h/8.8 | j/2.9 | — | 40 | q/1 | o/6.5 |
|    | IE | e/60.0 | f/25.0 | h/11.3 | j/3.8 | — | 80 | | |

[1]RE = Release end
[2]IE = Inner end

EXAMPLE 2

Sustained Release of Implants of the Invention in Pigs

Pigs are divided into groups of four animals. Throughout the test, all pigs are fed the same ration containing 20% w/w crude protein. The pigs are not treated for three days and daily porcine somatotropin blood levels are obtained for each group of animals. Then two implants, listed in Table II, are implanted in the ear of each pig. Somatotropin levels in the blood of the animals is determined by standard RIA techniques daily. The results of this experiment, summarized in Table III below, demonstrate the effectiveness of the compositions of the invention for increasing and maintaining elevated somatotropin levels in the blood for extended periods of time.

TABLE III

Average Plasma rpST Concentration (ng/mL by Radioimmunoassay) for Pig Experiments

| Time (Days) | Composition from Table II | | | | | |
|---|---|---|---|---|---|---|
| | 2 | 7 | 10 | 11 | 12 | 13 |
| −3 | 1.9 | 1.4 | 1.5 | 2.1 | 3.8 | 2.5 |
| −2 | 0.9 | 2.2 | 2.6 | 4.9 | 2.4 | 3.8 |
| −1 | 1.2 | 2.3 | 1.7 | 2.4 | 3.3 | 4.2 |
| 1 | 6.6 | 5.5 | 4.9 | 1.7 | 3.0 | 1.4 |
| 2 | 8.2 | 3.5 | 35.2 | 1.5 | 3.5 | 1.6 |

TABLE III-continued

Average Plasma rpST Concentration (ng/mL by Radioimmunoassay) for Pig Experiments

| Time (Days) | Composition from Table II | | | | | |
|---|---|---|---|---|---|---|
| | 2 | 7 | 10 | 11 | 12 | 13 |
| 3 | 9.8 | 13.9 | 97.1 | 2.6 | 3.8 | 3.2 |
| 4 | 6.3 | 11.3 | 60.9 | 1.9 | 3.2 | 2.4 |
| 5 | 3.4 | 17.6 | 56.4 | 1.5 | 18.9 | 8.6 |
| 6 | 20.1 | 16.2 | 474.8 | 11.2 | 61.2 | 17.6 |
| 7 | 26.4 | 20.6 | 242.6 | 3.3 | 40.3 | 22.9 |
| 8 | 26.1 | 20.0 | 110.6 | 118.1 | 35.4 | 41.3 |
| 9 | 50.0 | 19.4 | 70.7 | 87.0 | 19.7 | 43.0 |
| 10 | 42.9 | 25.9 | 45.4 | 56.6 | 30.0 | 55.0 |
| 11 | 26.1 | 35.7 | 82.4 | 44.3 | 15.7 | 32.5 |
| 12 | 16.0 | 34.2 | 47.1 | 34.8 | 22.7 | 35.3 |
| 13 | 26.2 | 29.8 | 52.1 | 40.1 | 6.7 | 25.0 |
| 14 | 19.9 | 31.4 | 28.8 | 54.4 | 8.0 | 39.8 |
| 15 | 10.2 | 25.3 | 21.3 | 25.9 | 4.8 | 20.0 |
| 16 | 8.8 | 20.7 | 19.7 | 31.3 | 4.7 | 12.5 |
| 17 | 13.4 | 10.5 | 6.8 | 29.2 | 4.9 | 10.2 |
| 18 | 8.0 | 15.4 | 7.8 | 18.5 | 4.0 | 10.0 |
| 19 | 32.1 | 34.4 | 10.0 | 16.1 | 3.8 | 5.3 |
| 20 | 5.8 | 9.4 | 8.2 | 14.9 | 2.8 | 6.8 |
| 21 | 9.6 | 13.6 | 9.9 | 8.7 | 2.7 | 3.1 |
| 22 | 15.1 | 11.2 | 5.7 | 7.4 | 35.6 | 7.1 |
| 23 | 60.8 | 7.1 | 6.0 | 15.9 | 12.8 | 4.3 |
| 24 | 4.9 | 7.6 | 12.6 | 11.2 | 4.0 | 4.4 |
| 25 | 8.4 | 7.0 | 5.4 | 5.4 | 2.3 | 3.4 |

TABLE III-continued

Average Plasma rpST Concentration (ng/mL by Radioimmunoassay) for Pig Experiments

| Time | Composition from Table II | | | | | |
|---|---|---|---|---|---|---|
| (Days) | 2 | 7 | 10 | 11 | 12 | 13 |
| 26 | 8.9 | 6.6 | 4.0 | 5.3 | 2.7 | 6.8 |
| 27 | 6.7 | 7.3 | 4.8 | 8.6 | 5.0 | 6.5 |

EXAMPLE 3

In Vitro Dissolution Evaluation of Implants

Two implants are placed in a plastic tube containing 10 mL of a phosphate buffer solution (pH 7.4, 100 nM NaCl, 50 mM $Na_2HPO_4/NaH_2PO_4$, 0.2% w/v Na azide) and the tube is placed in a water bath where the temperature of the water in the unit is maintained at 39° C. The tube is kept in the water bath for two days, then the solution is removed from the tube and analyzed for the appropriate somatotropin by HPLC and the solution is discarded. New phosphate buffer solution is added to the tube and the tube is placed into the water bath for three additional days and analyzed as described above. This procedure is repeated several times at various time intervals until the experiment is terminated. Table IV below summarizes the release rates of the appropriate somatotropin for several compositions listed in Table II.

TABLE IV

Release Rate (mg/day)

| Days | Composition | | |
|---|---|---|---|
| | 2 | 7 | 10 |
| 0–2 | 0.6 | 0.6 | 1.0 |
| 2–5 | 3.8 | 7.6 | 11.4 |
| 5–9 | 7.2 | 7.0 | 6.9 |
| 9–12 | 5.3 | 3.4 | 4.2 |
| 12–16 | 2.7 | 1.7 | 2.1 |
| 16–19 | 1.6 | 1.3 | 1.8 |
| 19–23 | 1.3 | 0.9 | 1.4 |
| 23–28 | 0.9 | 0.6 | 1.0 |

Following the above procedure but analyzing the solutions for the appropriate somatotropin at different time intervals than described above gives the release rates summarized below in Tables V, VI and VII.

TABLE V

Release Rate (mg/day)

| Days | Composition | |
|---|---|---|
| | 11 | 13 |
| 0–1 | 0.1 | 0.0 |
| 1–2 | 2.5 | 1.4 |
| 2–5 | 7.0 | 3.9 |
| 5–9 | 5.9 | 6.4 |
| 11–12 | 3.9 | 4.3 |
| 12–16 | 2.5 | 2.5 |
| 16–19 | 1.7 | 1.3 |
| 19–22 | 1.4 | 1.1 |

TABLE V-continued

Release Rate (mg/day)

| Days | Composition | |
|---|---|---|
| | 11 | 13 |
| 22–26 | 1.0 | 1.1 |
| 26–28 | 0.8 | 0.6 |

TABLE VI

Release Rate (mg/day)

| Days | Composition 12 |
|---|---|
| 0–1 | 0.5 |
| 1–3 | 2.0 |
| 3–7 | 5.1 |
| 7–10 | 7.1 |
| 10–14 | 3.9 |
| 14–17 | 1.9 |
| 17–21 | 1.3 |
| 21–24 | 0.9 |
| 24–28 | 0.7 |

TABLE VII

Release Rate (mg/day)

| Days | Composition | | |
|---|---|---|---|
| | 15 | 16 | 17 |
| 0–1 | 0.0 | 0.0 | 0.0 |
| 1–2 | 2.2 | 0.7 | 0.7 |
| 2–5 | 1.5 | 3.0 | 3.3 |
| 5–9 | 3.9 | 4.4 | 4.5 |
| 9–12 | 4.6 | 4.1 | 2.6 |
| 12–16 | 2.4 | 2.3 | 1.1 |
| 16–20 | 1.5 | 1.6 | 0.7 |
| 20–23 | 0.9 | 1.2 | 0.4 |
| 23–26 | 0.9 | 1.1 | 0.3 |

Additionally, following the above procedure but using three implants gives the release rates summarized below in Table VIII.

TABLE VIII

Release Rate (mg/day)

| Days | Composition 14 |
|---|---|
| 0–1 | 0.0 |
| 1–4 | 1.4 |
| 4–7 | 3.9 |
| 7–11 | 4.7 |
| 11–14 | 3.3 |
| 14–18 | 1.9 |
| 18–21 | 1.5 |
| 21–34 | 0.8 |

EXAMPLE 4

In Vivo Evaluation of Implants

In this study, pigs are divided into groups of seven animals. Each animal receives three implants having core weights of 60 mg, 90 mg and 90 mg. The 60 mg core is given a thinner coating of about 4 mil (approximately equivalent to ¹⁄₁₀₀₀ inch) which provides an implant comprising a core of about 82% w/w and a coating of about 18% w/w. The coating on the implant having the 90 mg core is about 9.2 mil. The latter implant comprises a core of about 61% w/w and a coating of about 39% w/w.

The formulation of the core mixture is as follows:

| Ingredient | Amount (% w/w) |
|---|---|
| Porcine somatotropin, anhydrous | 50.74 |
| Water of hydration | 4.4 |
| Sodium phosphate | 5.02 |
| Sodium borate (decahydrate) | 1.25 |
| Glyceryl trimyristate | 33.63 |
| Microcrystalline talc | 4.96 |

The composition of the coating is as follows:

| Ingredient | Amount (% w/w) |
|---|---|
| Poly(ethylacrylate, methyl-methacrylate) copolymer | 75.00 |
| Microcrystalline talc | 25.00 |

The implants are made using the following steps:

1. Spray drying procedure: Lyophilized recombinant porcine somatotropin (A6TS11R+E34 rpST) is dissolved in purified water and then a solution of 4% w/v sodium phosphates (a mixture of approximately 1.1 parts of monobasic sodium phosphate and 1 part of dibasic sodium phosphate) and 1% w/v sodium tetraborate decahydrate is added by gentle mixing to achieve a final pH of about 7.4. The liquid composition contains 8.9 parts pST, 1.1 parts buffer and 90 parts water. This solution is filtered with a membrane filter having the pore size of 0.45μ. The filtered solution is spray dried on a Buchi 190 laboratory sized spray dryer with the operating settings of 10 mL/min feed rate, about 130° C. outlet temperature and about 65° C. inlet temperature. The powder product is identified as spray-dried pST.

2. pST Granulation Procedure: A jacketed glass mixing bowl is maintained at approximately 68° C. to melt glyceryl trimyristate. Then spray-dried pST and talc is added and melt blended thoroughly with the fat. The mixture is densified by slugging in a Stokes-Merrill tablet press (VersaPress model 900-560) using ⁷⁄₁₆" dies with flat faced beveled edge punches and a compression force at about 1.5 tons. The slugs are milled using a Thomas-Wiley Intermediate Mill with a 20 mesh screen (841μ) to a collection vessel. The resultant powder is composed of coarse particles of varying size.

3. Implant Production: Implants are made on a Stokes-Merrill tablet press (Model 900-560). The dies are ⁵⁄₃₂" diameter. The bottom punch is a standard concave. The top punch is specifically designed as described in Example 1 above. The implants are prepared by manual filling of the die then compressing the implants at approximately 1000 lb compression force. Implants are made in two weight ranges: 58–62 mg and 88–92 mg.

4. Partial coating: Implants are partially coated in the UNIGlatt coater with a Wurster insert without the partition. The coating suspension consists of 30% w/w solids. Of the solids, 75% w/w is poly(ethylacrylate, methylmethacrylate) copolymer (EUDRAGIT® NE30D as the suspension, commercially available from Rohm Pharma GmbH) and 25% w/w microcrystalline talc. The coating conditions are set at an initial product load of 800 g, inlet temperature at 25°–32° C., outlet temperature at 22°–26° C. and feed application rate of 6–8 mL/min. Implants that are approximately 60 mg are treated so as to receive about 4 mil of coating thickness. Implants that are approximately 90 mg are treated so to obtain a coating thickness of about 9.2 mil. An aqueous dispersion coating of calcium chlortetracycline is added over the EUDRAGIT® NE/talc coating to reduce the incidence of infection at the site of implantation.

This experiment is conducted in catheterized pigs which are held in metabolism cages to limit their movement and facilitate daily blood samples from which to analyze pST concentration (by standard radioimmunoassay, RIA) and blood urea nitrogen levels (BUN). Throughout the test, all pigs are fed the same ration containing 20% crude protein. The pigs are not treated for three days and daily porcine somatotropin blood levels are obtained for each group of animals. Three implants having core weights of 60 mg, 90 mg and 90 mg are implanted in the ear (same implant site) of each pig. The somatotropin and BUN levels are measured in plasma.

The blood levels of the porcine somatotropin (PST) and the blood urea nitrogen (BUN) are set forth below in Table IX and in the graph identified as FIG. 1. The data show very consistent blood levels of pST in the animals for extended periods of time. The results of the experiment demonstrate that the implants of the present invention provide rather uniform levels of pST in the blood for about three weeks and then a slow decline in the fourth week. The variability in the pigs is given by the columns in Table IX showing the mean plus the standard deviation to the mean minus the standard deviation. Also shown are mean BUN levels. BUN is a biological indicator which is depressed under the influence of increased pST levels. BUN is observed in FIG. 1 to be roughly inversely related to pST levels.

TABLE IX

Average Plasma pST Concentration and BUN Levels in Pigs

| Time (Day) | Geometric Mean pST (ng/mL) | Mean pST (+STD) | Mean pST (−STD) | Mean BUN (mg/dl) |
|---|---|---|---|---|
| −2 | 2.73 | 3.57 | 1.86 | 14.00 |
| −1 | 3.31 | 4.92 | 1.89 | 13.70 |
| 0¹ | 3.03 | 4.30 | 1.86 | 14.60 |
| 1 | 3.04 | 4.13 | 1.97 | 13.30 |
| 2 | 2.48 | 4.40 | 1.10 | 13.60 |
| 3 | 8.84 | 31.78 | 1.45 | 11.60 |
| 4 | 10.27 | 16.57 | 5.22 | 8.60 |
| 5 | 8.71 | 11.15 | 6.15 | 9.00 |
| 6 | 7.19 | 11.28 | 3.80 | 8.43 |
| 7 | 13.12 | 25.58 | 5.10 | 6.43 |
| 8 | 11.93 | 25.30 | 4.12 | 7.60 |
| 9 | 10.28 | 17.72 | 4.76 | 7.90 |
| 10 | 10.33 | 15.79 | 5.67 | 8.30 |
| 11 | 9.42 | 16.74 | 4.18 | 10.60 |
| 12 | 9.29 | 14.86 | 4.78 | 9.30 |
| 13 | 11.64 | 21.12 | 5.01 | 9.60 |
| 14 | 10.71 | 18.33 | 5.01 | 9.00 |
| 15 | 9.35 | 15.35 | 4.64 | 9.10 |
| 16 | 8.67 | 15.36 | 3.86 | 9.30 |
| 17 | 8.54 | 13.61 | 4.41 | 8.70 |
| 18 | 9.95 | 21.09 | 3.44 | 9.30 |
| 19 | 7.67 | 11.62 | 4.27 | 9.60 |
| 20 | 8.07 | 12.12 | 4.54 | 10.30 |
| 21 | 6.72 | 11.17 | 3.27 | 11.60 |
| 22 | 5.26 | 7.85 | 2.98 | 11.90 |
| 23 | 4.81 | 7.77 | 2.44 | 11.90 |

TABLE IX-continued

Average Plasma pST Concentration and BUN Levels in Pigs

| Time (Day) | Geometric Mean pST (ng/mL) | Mean pST (+STD) | Mean pST (−STD) | Mean BUN (mg/dl) |
|---|---|---|---|---|
| 24 | 4.15 | 6.18 | 2.37 | 12.30 |
| 25 | 4.21 | 6.36 | 2.35 | 13.60 |
| 26 | 4.11 | 6.24 | 2.27 | 14.00 |
| 27 | 3.70 | 4.82 | 2.55 | 14.10 |
| 28 | 3.57 | 4.65 | 2.46 | 14.70 |
| 29 | 4.23 | 5.61 | 2.84 | 13.00 |
| 30 | 3.68 | 4.92 | 2.44 | 13.60 |

[1]Day of implantation of three implants per pig: (1) 4 mil coat, 60 mg implant; (2) 9.2 mil coat, 90 mg implant; and (3) 9.2 mil coat, 90 mg implant.

EXAMPLE 5

In Vivo Evaluation of Implants

In this study, each animal in a group of six receives three implants having core weights of 60 mg, 90 mg and 90 mg which are prepared and evaluated as described in Example 4 above. The implant with the 60 mg core is again given a thinner coating of about 4 mil, but the coating on the implant having the 90 mg core is about 5.9 mil. Also, no antibiotic is added over the EUDRAGIT® NE/talc coating.

The results of this experiment demonstrate good blood urea nitrogen values in that they remain depressed in comparison to control values (e.g., average of days −2 to 0) throughout the four weeks.

Figure 2:
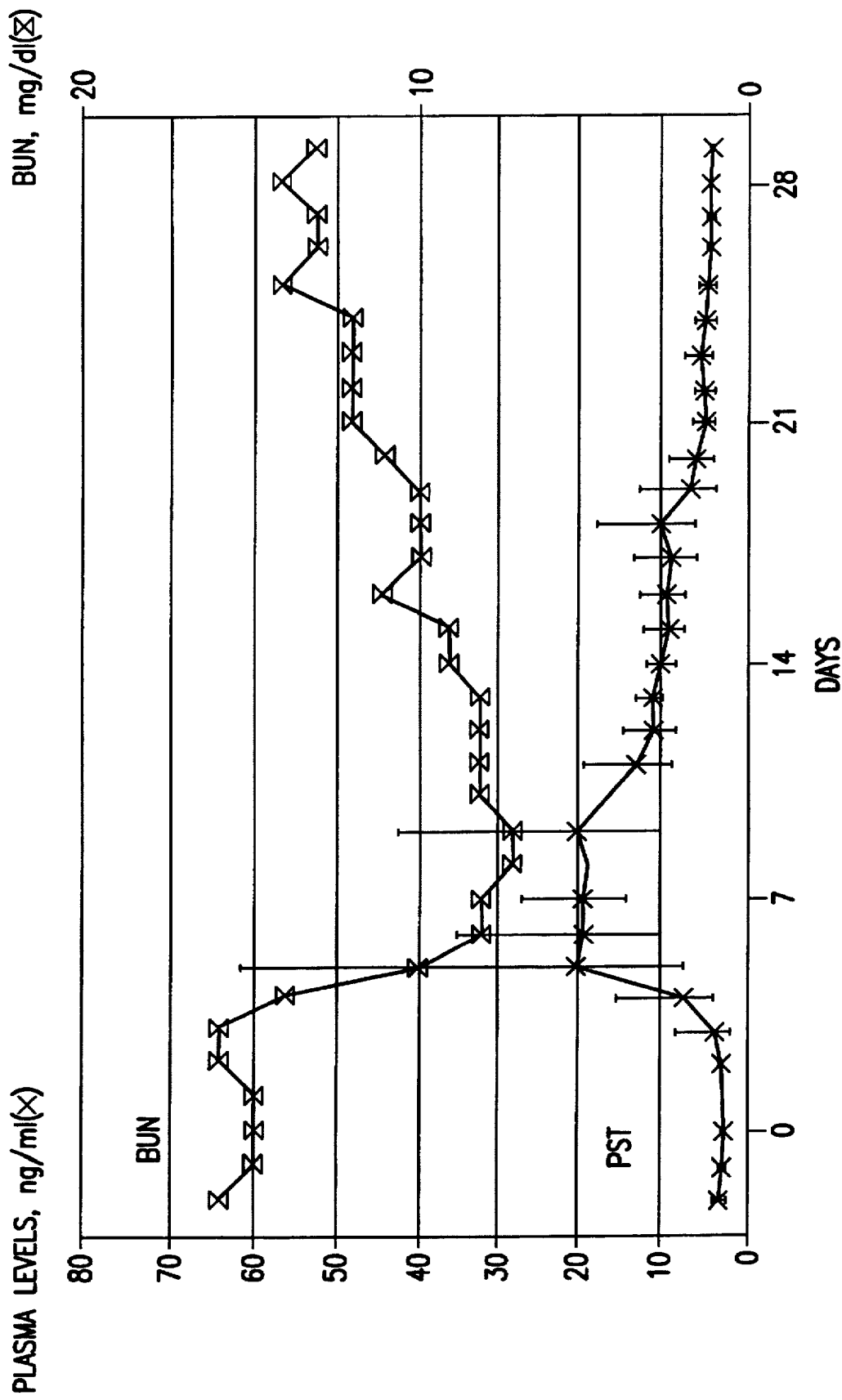
FIG. 2 shows the measurement of the plasma levels of recombinant porcine somatotropin (A6TS11R+E34 rpST) and blood urea nitrogen (BUN) in a group of six pigs. Pigs are implanted on Day 0 with three implants having core weights of 60 mg, 90 mg and 90 mg, and a coating thickness of 4 mil, 5.9 mil and 5.9 mil, respectively. The data represent the geometric mean plasma levels of the rpST along with the variability in the pigs expressed as mean plus or minus the standard deviation. Also shown are mean BUN levels taken from the blood samples of each of the animals.

The data of the blood levels of the porcine somatotropin (PST) and the blood urea nitrogen (BUN) are set forth below in Table X and in the graph identified as FIG. 2. The somatotropin and BUN levels are measured in plasma.

TABLE X

Average Plasma pST Concentration and BUN Levels in Pigs

| Time (Day) | Geometric Mean pST (ng/mL) | Mean pST (+STD) | Mean pST (−STD) | Mean BUN (mg/dl) |
|---|---|---|---|---|
| −2 | 2.71 | 3.68 | 2.00 | 16.00 |
| −1 | 2.33 | 2.83 | 1.92 | 15.00 |
| 0[1] | 2.22 | 2.59 | 1.91 | 15.00 |
| 1 | 2.52 | 2.78 | 2.28 | 15.00 |
| 2 | 2.24 | 2.79 | 1.80 | 16.00 |
| 3 | 3.23 | 8.02 | 1.30 | 16.00 |
| 4 | 7.22 | 15.23 | 3.42 | 14.00 |
| 5 | 20.77 | 61.75 | 6.98 | 10.00 |
| 6 | 18.95 | 35.34 | 10.16 | 8.00 |
| 7 | 19.45 | 26.74 | 14.15 | 8.00 |
| 8 | 18.43 | 26.68 | 12.73 | 7.00 |
| 9 | 20.39 | 42.44 | 9.80 | 7.00 |
| 10 | 15.64 | 22.07 | 11.09 | 8.00 |
| 11 | 12.74 | 19.34 | 8.39 | 8.00 |
| 12 | 10.67 | 14.28 | 7.97 | 8.00 |
| 13 | 10.99 | 12.78 | 9.45 | 8.00 |
| 14 | 10.11 | 11.80 | 8.65 | 9.00 |
| 15 | 9.02 | 11.90 | 6.84 | 9.00 |
| 16 | 9.16 | 12.42 | 6.76 | 11.00 |
| 17 | 8.24 | 12.96 | 5.24 | 10.00 |
| 18 | 9.70 | 17.30 | 5.44 | 10.00 |
| 19 | 6.07 | 12.35 | 2.99 | 10.00 |
| 20 | 5.36 | 8.85 | 3.25 | 11.00 |
| 21 | 4.19 | 5.72 | 3.07 | 12.00 |
| 22 | 4.28 | 5.64 | 3.25 | 12.00 |
| 23 | 4.73 | 6.72 | 3.32 | 12.00 |
| 24 | 4.08 | 5.54 | 3.01 | 12.00 |
| 25 | 3.87 | 4.98 | 3.02 | 14.00 |
| 26 | 3.37 | 3.97 | 2.86 | 13.00 |
| 27 | 3.47 | 4.13 | 2.92 | 13.00 |
| 28 | 3.73 | 4.39 | 3.16 | 14.00 |
| 29 | 3.32 | 3.83 | 2.88 | 13.00 |

[1]Day of implantation of three implants per pig: (1) 4 mil coat, 60 mg implant; (2) 5.9 mil coat, 90 mg implant; and (3) 5.9 mil coat, 90 mg implant.

In the foregoing, there has been provided a detailed description of particular embodiments of the present invention for the purpose of illustration and not limitation. It is to be understood that all other modifications, ramifications, and equivalents obvious to those having skill in the art based on this disclosure are intended to be included within the scope of the invention as claimed.

What is claimed is:

1. An implant for the parenteral administration of an essentially uniform and continuous amount of a biologically active protein, a peptide or a polypeptide selected from the group consisting of a growth factor, a biologically active fragment thereof and a derivative thereof over an extended period of time which comprises a compacted, indented and partially coated composition containing from one to three layers of a homogeneous core mixture comprising about 20% to about 80% of the growth factor, the biologically active fragment or the derivative; about 10% to about 75% of a fat, a wax or a mixture thereof; 0% to about 25% of a buffer, a salt, a sugar or a mixture thereof; and 0% to about 15% of a filler, on a weight basis of the total weight of the core mixture.

2. The implant according to claim 1, wherein the buffer, the salt, the sugar or the mixture thereof is present in the amount of about 2% to about 25%.

3. The implant according to claim 2, wherein the growth factor is a somatotropin.

4. The implant according to claim 3, wherein the somatotropin is selected from the group consisting of porcine, ovine, equine, bovine, avian and human somatotropins.

5. The implant according to claim 4, wherein the somatotropin is a porcine somatotropin selected from the group consisting of E34 rpST, I122L+E34 rpST, A6TS11R+E34 rpST and carbimidomethyl rpST.

6. The implant according to claim 1, which comprises about 45% to about 65% of the growth factor, the biologically active fragment or the derivative; about 15% to about 50% of the fat, the wax or the mixture thereof; about 2% to about 20% of the buffer, the salt or the mixture thereof; and about 1% to about 15% of the filler, on a weight basis of the total weight of the core mixture.

7. The implant according to claim 6, wherein the fat is selected from the group consisting of glyceryl trimyristate, glyceryl tripalmitate and glyceryl tristearate; the buffer is selected from the group consisting of sodium borate, sodium tartrate, sodium citrate, sodium carbonate, monobasic sodium phosphate, dibasic sodium phosphate and a mixture thereof; and the filler is selected from the group consisting of talc; and fumed silica.

8. The implant according to claim 7, wherein the growth factor is a porcine somatotropin selected from the group consisting of E34 rpST, I122L+E34 rpST, A6TS11R+E34 rpST and carbimidomethyl rpST.

9. The implant according to claim 8, wherein the porcine somatotropin is A6TS11R+E34 rpST; the fat is glyceryl trimyristate; the buffer is a mixture of sodium borate, monobasic sodium phosphate and dibasic sodium phosphate; and the filler is talc.

10. The implant according to claim 6, wherein the composition provides a first layer, a middle layer and a third layer of the homogeneous core mixture in which the third layer surrounds and is contiguous with the indentation, the middle layer is contiguous with the first and third layers, and the first layer is contiguous with the middle layer and contains a greater amount of the growth factor, the biologically active fragment or the derivative than the third layer.

11. The implant according to claim 1, wherein the partial coating comprises about 65% to about 85% of a semipermeable material; about 15% to about 35% of a tackiness control agent; 0% to about 3% of a cellulose; 0% to about 20% of a plasticizer; and 0% to about 20% of a filler, on a weight basis of the total dry weight of the coating; the partial coating is present on the implant in the amount of about 5% to about 50%, on a weight basis of the total weight of the implant; and the partial coating has a thickness of about 0.5 mil to about 25 mil.

12. The implant according to claim 11, wherein an antibiotic is applied to the partial coating.

13. The implant according to claim 11, wherein the semipermeable material is a semipermeable polymer selected from the group consisting of a methacrylate ester copolymer and a methacrylic acid copolymer.

14. The implant according to claim 13, wherein the semipermeable polymer is the methacrylate ester copolymer, said methacrylate ester copolymer is a poly (ethylacrylate, methylmethacrylate) copolymer and the tackiness control agent is talc.

15. The implant according to claim 6, wherein the partial coating comprises about 70% to about 80% of a semipermeable material; about 20% to about 30% of a tackiness control agent; 0% to about 3% of a cellulose; 0% to about 20% of a plasticizer; and 0% to about 20% of a filler, on a weight basis of the total dry weight of the coating; the partial coating is present on the implant in the amount of about 10% to about 39%, on a weight basis of the total weight of the implant; and the partial coating has a thickness of about 2 mil to about 20 mil.

16. The implant according to claim 15, wherein an antibiotic is applied to the partial coating.

17. The implant according to claim 15, wherein the semipermeable material is a semipermeable polymer selected from the group consisting of a methacrylate ester copolymer and a methacrylic acid copolymer.

18. The implant according to claim 17, wherein the semipermeable polymer is the methacrylate ester copolymer and said methacrylate ester copolymer is a poly (ethylacrylate, methylmethacrylate) copolymer.

19. The implant according to claim 18, wherein the tackiness control agent is talc.

20. The implant according to claim 19, wherein the core mixture comprises the growth factor; the growth factor is a somatotropin selected from the group consisting of porcine, ovine, equine, bovine, avian and human somatotropins; the fat is selected from the group consisting of glyceryl trimyristate, glyceryl tripalmitate and glyceryl tristearate; the buffer is selected from the group consisting of sodium borate, sodium tartrate, sodium citrate, sodium carbonate, monobasic sodium phosphate, dibasic sodium phosphate and a mixture thereof; and the filler is selected from the group consisting of talc and fumed silica.

21. The implant according to claim 20, wherein the somatotropin is a porcine somatotropin selected from the group consisting of E34 rpST, I122L+E34 rpST, A6TS11R+E34 rpST and carbimidomethyl rpST.

22. The implant according to claim 21, wherein the porcine somatotropin is A6TS11R+E34 rpST; the fat is glyceryl trimyristate; the buffer is a mixture of sodium borate, monobasic sodium phosphate and dibasic sodium phosphate; and the filler is talc.

23. The implant according to claim 22, wherein the talc is microcrystalline talc and the partial coating has a thickness of about 2 mil to about 10 mil.

24. An implant for the parenteral administration of an essentially uniform and continuous amount of a somatomedin over an extended period of time which comprises a compacted, indented and partially coated composition containing from one to three layers of a homogeneous core mixture comprising about 20% to about 80% of the somatomedin; about 10% to about 75% of a fat, a wax or a mixture thereof; 0% to about 25% of a buffer, a salt, a sugar or a mixture thereof; and 0% to about 15% of a filler, on a weight basis of the total weight of the core mixture.

25. A method for elevating and maintaining elevated blood levels of a growth factor, a biologically active fragment thereof or a derivative thereof, increasing growth rate, improving feed efficiency, improving lean meat to fat ratio or increasing milk production in lactating animals which comprises parenterally administering to an animal from one to three implants as described in claim 1.

26. A method for elevating and maintaining elevated blood levels of a somatotropin, increasing growth rate, improving feed efficiency, improving lean meat to fat ratio or increasing milk production in lactating animals which comprises parenterally administering to an animal from one to three implants as described in claim 3.

27. The method according to claim 26, which comprises administering the implant in which the somatotropin is a porcine somatotropin selected from the group consisting of E34 rpST, I122L+E34 rpST, A6TS11R+E34 rpST and carbimidomethyl rpST.

28. A method for elevating and maintaining elevated blood levels of a growth factor, a biologically active fragment thereof or a derivative thereof, increasing growth rate, improving feed efficiency, improving lean meat to fat ratio or increasing milk production in lactating animals which comprises parenterally administering to an animal from one to three implants as described in claim 6.

29. The method according to claim 28, which comprises administering the implant in which the growth factor is a somatotropin.

30. The method according to claim 29, wherein the somatotropin is selected from the group consisting of porcine, ovine, equine, bovine, avian and human somatotropins.

31. The method according to claim 30, wherein the somatotropin is a porcine somatotropin selected from the group consisting of E34 rpST, I122L+E34 rpST, A6TS11R+E34 rpST and carbimidomethyl rpST.

32. A method for elevating and maintaining elevated blood levels of a growth factor, a biologically active fragment thereof or a derivative thereof, increasing growth rate, improving feed efficiency, improving lean meat to fat ratio or increasing milk production in lactating animals which comprises parenterally administering to an animal from one to three implants as described in claim 11.

33. A method for elevating and maintaining elevated blood levels of a growth factor, a biologically active fragment thereof or a derivative thereof, increasing growth rate, improving feed efficiency, improving lean meat to fat ratio or increasing milk production in lactating animals which comprises parenterally administering to an animal from one to three implants as described in claim 15.

34. A method for elevating and maintaining elevated blood levels of a somatotropin, increasing growth rate, improving feed efficiency, improving lean meat to fat ratio or increasing milk production in lactating animals which comprises parenterally administering to an animal from one to three implants as described in claim 20.

35. A method for elevating and maintaining elevated blood levels of A6TS11R+E34 rpST, increasing growth rate, improving feed efficiency, improving lean meat to fat ratio or increasing milk production in lactating animals which comprises parenterally administering to an animal from one to three implants as described in claim 22.

36. A method for elevating and maintaining elevated blood levels of A6TS11R+E34 rpST, increasing growth rate, improving feed efficiency, improving lean meat to fat ratio or increasing milk production in lactating animals which comprises parenterally administering to an animal from one to three implants as described in claim 23.

37. A method for elevating and maintaining elevated blood levels of a somatomedin, increasing growth rate, improving feed efficiency, improving lean meat to fat ratio or increasing milk production in lactating animals which comprises parenterally administering to an animal from one to three implants as described in claim 24.

38. The method according to claim 29, which comprises parenterally administering three implants simultaneously to the animal.

39. The method according to claim 33, which comprises parenterally administering three implants simultaneously to the animal.

40. The method according to claim 35, which comprises parenterally administering three implants simultaneously to the animal.

* * * * *